(12) United States Patent
Huland

(10) Patent No.: US 9,028,808 B2
(45) Date of Patent: May 12, 2015

(54) METHODS FOR TREATING NICOTINE ADDICTION AND REDUCING FOOD CONSUMPTION

(75) Inventor: Edith Huland, Hamburg (DE)

(73) Assignee: Immunservice GmbH, Hamburg (DE)

( * ) Notice: Subject to any disclaimer, the term of this patent is extended or adjusted under 35 U.S.C. 154(b) by 0 days.

(21) Appl. No.: 13/574,106

(22) PCT Filed: Jan. 27, 2011

(86) PCT No.: PCT/EP2011/051106
§ 371 (c)(1),
(2), (4) Date: Oct. 11, 2012

(87) PCT Pub. No.: WO2011/092231
PCT Pub. Date: Aug. 4, 2011

(65) Prior Publication Data
US 2013/0028861 A1   Jan. 31, 2013

Related U.S. Application Data

(60) Provisional application No. 61/299,131, filed on Jan. 28, 2010.

(30) Foreign Application Priority Data

Jan. 28, 2010   (EP) ...................................... 1015197

(51) Int. Cl.
*A61K 38/20* (2006.01)
*A61K 45/00* (2006.01)
*A61K 9/72* (2006.01)
*C07K 14/55* (2006.01)
*A61K 38/21* (2006.01)
*A61K 9/00* (2006.01)

(52) U.S. Cl.
CPC ............... *A61K 38/20* (2013.01); *A61K 9/0019* (2013.01); *A61K 9/007* (2013.01); *A61K 9/0078* (2013.01); *A61K 38/2013* (2013.01); *A61K 38/21* (2013.01); *A61K 38/212* (2013.01); *Y10S 514/958* (2013.01)

(58) Field of Classification Search
None
See application file for complete search history.

(56) References Cited

U.S. PATENT DOCUMENTS

| 5,399,341 A | 3/1995 | Huland et al. |
| 5,780,012 A | 7/1998 | Huland et al. |

FOREIGN PATENT DOCUMENTS

| EP | 0462305 | 11/1994 |
| RU | 2290947 | 1/2005 |

OTHER PUBLICATIONS

Gu, J., et al. Suppression of morphine withdrawal syndrome by interleukin-2 and its gene. NeuroReport, 2005, vol. 16, p. 387-391.*
http://www.asam.org/for-the-public/definition-of-addiction. American Society of Addiction Medicine, definition of "Addiction", Apr. 2011.*
Cesario T.C., et al. Functional, biochemical, and histopathologic consequences of high-dose interleukin-2 administration in rats. J. Lab. Clin. Med., 1991, vol. 118(1), p. 81-88.*
Dafny et al., "Interferon modifies morphine withdrawal phenomena in rodents," *Neuropharmacology*, 22(5):647-651, 1983.
Fomina et al., "Interferon and interleukin-2 as modulators of alcohol behavioral reactions in C57B1/6 mice," *European Neuropsychopharmacology*, 6:S4-132, 1996.
Fomina et al., "The effects of interferon on drug addiction," *International Journal of Neuropsychopharmacology*, 7(Supp2):S317-S318, 2004.
Avila et al., "Immune cell activity during the initial stages of withdrawal from chronic exposure to cocaine or morphine," *Journal of Neuroimmunology*, 147 (2004), 109-113.
Friedman et al., "Addictive drugs and their relationship with infectious diseases," *FEMS Immunol Med Microbiol*, 47 (2006) 330-342.
Gu et al, "Suppression of morphine withdrawal syndrome by interleukin-2 and its gene," *Neuroreport*, 16(4):387-391, 2005.
Hughes, "Should criteria for drug dependence differ across drugs?," *American Psychiatric Association*, Journal compilation, Addiction 101 (Suppl. 1 ), 2006, 134.141.
Huland, "Interleukin-2 and Cancer Physiological and Pharmacological Uses," *Folia Biologica*, (Praha) 47, 2001, 111-112.
Lesch, "Addiction in DSM V and ICD-11 State of the Art," *Neurological Psychiatry*,77 , 2009, 507-512.
Loppow et al., "Interleukin-2 Inhalation Therapy Temporarily Induces Asthma-like Airway Inflammation," *European Journal of Medical Research*, 12 (2007), 1-7.
Lorenz et al., "Phase I Trial of Inhaled Natural Interleukin 2 for Treatment of Pulmonary Malignancy: Toxicity, Pharmacokinetics, and Biological Effects," *Clinical Cancer Research*, vol. 2, Jul. 1996, pp. 1115-1122.
Lüscher et al., "The Mechanistic Classification of Addictive Drugs," *PLoS Medicine*, vol. 3, Nov. 2006, 2005-2010.
PCT International Preliminary Report on Patentability issued in International Application No. PCT/EP2011/051103, issued Jul. 31, 2012.
PCT International Search Report issued in International Application No. PCT/EP2011/051106, mailed May 30, 2011.
Radzius et al., "Nicotine dependence criteria of the DIS and DSM-III-R: A factor analysis," *Nicotine & Tobacco Research*, vol. 6 (2), Apr. 2004, 303-308.

(Continued)

Primary Examiner — Robert Landsman
Assistant Examiner — Bruce D Hissong
(74) Attorney, Agent, or Firm — Parker Highlander PLLC

(57) ABSTRACT

The present invention relates to a cytokine for use in the treatment and/or control of dependent and/or addictive behavior, in particular addiction and/or dependency to nicotine, food addiction, alcohol addiction and/or sex addiction. The present invention also relates to treatment and/or control of withdrawal and/or symptoms of withdrawal from an addiction, in particular nicotine addiction, food addiction, alcohol addiction and/or sex addiction. The present invention further relates to the induction of loss of interest or aversion to the addictive substance or behavior, such as nicotine, over-indulgence in high-calorie, high-fat foods, and to other behaviors or addictions that are hazardous to the health.

17 Claims, No Drawings

(56) References Cited

OTHER PUBLICATIONS

Rose, "Multiple brain pathways and receptors underlying tobacco addiction," *Biochemical Pharmacology*, 74 (2007), 1263-1270.

Saunders and Schuckit, "The development of a research agenda for substance use disorders diagnosis in the Diagnostic and Statistical Manual of Mental Disorders, fifth edition (DSM-V)," *American Psychiatric Association*, Journal compilation, Addiction 101 (Suppl. 1), 2006, 1-5.

de la Rosette et al., "Renal Cell Cancer—Diagnosis and Therapy," eds Springer, Chapter 11a Immunotherapy, 2008. Print.

Thielmann, et al., "Increased health hazards due to additives of tobacco products—consequences for product regulation", DKFZ 2005, 1-12.

Blum et al., "Neurogentics of dopaminergic receptor super-sensitivity in activation of brain reward circuitry and relapse: proposing 'Deprivation-Amplification Relapse Therapy' (DART)", *Postgrad Med.*, 121(6):176-796, 2009.

Huland et al., "Inhaled interleukin-2 in combination with low-dose systemic interleukin-2 and interferon α in patients with pulmonary metastatic renal-cell carcinoma: effectiveness and toxicity of mainly local treatment", *J Cancer Res Clin Oncol.*, 120:221-228, 1994.

Huland et al., "Interieukin-2 by inhalation: local therapy for metastatic renal cell carcinoma", *The Journal of Urology*, 147:344-348, 1992.

Volkow and Wise, "How can drug addiction help us understand obesity?", *Nature Neuroscience*, 8(5):555-560, 2005.

\* cited by examiner

METHODS FOR TREATING NICOTINE ADDICTION AND REDUCING FOOD CONSUMPTION

The present application is a national phase application under 35 U.S.C. §371 of International Application No. PCT/EP2011/051106 filed Jan. 27, 2011 which claims priority to U.S. Provisional Application No. 61/299,131 filed Jan. 28, 2010 and European Patent Application 10151979 filed Jan. 28, 2010 the entire text and figures of which disclosures are incorporated herein by reference without disclaimer.

The present invention relates to a cytokine for use in the treatment and/or control of dependent and/or addictive behavior, in particular addiction and/or dependency to nicotine, food addiction, alcohol addiction and/or sex addiction. The present invention also relates to treatment and/or control of withdrawal and/or symptoms of withdrawal from an addiction, in particular nicotine addiction, food addiction, alcohol addiction and/or sex addiction. The present invention further relates to the induction of loss of interest or aversion to the addictive substance or behavior, such as nicotine, over-indulgence in high-calorie, high-fat foods, and to other behaviors or addictions that are hazardous to the health.

BACKGROUND

I. Nicotine Addiction

People who smoke become dependent on nicotine, a substance contained in tobacco, which affects the nervous system where it binds to receptors (nicotinic cholinergic receptor) and triggers the release of the messenger dopamine which contributes to the sense of well-being connected with smoking. It is accepted that nicotine is an addictive drug that alters brain mechanisms manifesting in dependency and, ultimately, withdrawal symptoms upon its discontinuation of use (NIDA Research Report Series Tobacco Addiction (2009)). Nicotine has been classified as a Class II drug, which mediates its effects via ionotropic receptors (Lëscher, C. and Ungless, M. A., PLoS 3 (11): 2005-2010 (2006). Alcohol is also classified as a Class II drug. The World Health Organization (WHO), which uses the International Classification of Diseases (ICD), classifies tobacco abuse as a mental and behavioral disorder attributed to a psychoactive substance (classification F17): The Diagnostic and Statistical Manual of Mental Disorders (DSM) also includes a diagnose for nicotine dependence (see, e.g. Hughes, J. R. Addiction 101 (Suppl. 1): 134-141 (2006). Further, nicotine addiction has been described as a complex neuropsycopharmacological disorder that may require addressing multiple molecular and brain components to free those suffering from this addiction (Rose, J., Biochem. Pharma. 74: 1263-1270 (2007)).

The European Commission estimate that 650,000 Europeans (i.e. 1 out of 7) die early each year due to diseases caused by smoking and that another 13 million suffer from serious, chronic diseases due to smoking. 29% of Europeans (25 member states, 2002-2003) are smokers. Surveys show that 70% are interested in giving up smoking, 40% try to stop smoking, but only 3.5% succeed without support. Often relapses occur within days or weeks; most smokers make several attempts, usually in intervals of 2 to 3 years.

Smoking cigarettes, cigars or pipes and chewing or sniffing tobacco leads to the intake of nicotine, which represents the essential addictive substance, and to the intake of further toxins. Nicotine is one of the substances with the highest addiction potential when measured against illegal drugs, such as, e.g. cocaine, and apart from a learning effect, is also responsible for the dependence on tobacco products.

Withdrawal symptoms, which can be very distinct, occur from the first day of smoking cessation. These symptoms, which can include depression, downheartedness, clear difficulties in concentrating, restlessness, increased appetite, trembling, sweating and sleep disorder, cause considerable stress with the dependent smoker and a strong desire for cigarettes, which counteracts the endeavors to stop smoking.

The acute withdrawal symptoms are often described as "physical dependence". By slowly withdrawing nicotine, be it in the form of tobacco products or nicotine preparations, the symptoms subside relatively quickly (after 3 weeks at the latest). Slight withdrawal symptoms, however, can last up to several months.

The strong desire for cigarettes and concrete situations of temptation are by far more difficult to overcome. Cigarette smoking is one of the most complicated and most difficult behavior patterns to break. Most people make several attempts (three to five times) before they succeed. It can take months or even years to achieve abstinence.

Nicotine substitution in many different variations (e.g. as chewing gum, lozenges for sucking, as an electronic cigarette or as nose spray) reduces these acute symptoms and it is used mostly to support the withdrawal from smoking cigarettes.

Evidently, apart from direct dependence on nicotine, there is another addiction potential, often described as psychological dependence, which is due to behavior patterns practiced over years (such as, e.g., reaching out for the cigarette package, lightening of a cigarette, the association with a break, a coffee, etc.). This supplementary addiction potential also serves as an explanation for the failure of many therapies with nicotine substitutes. Moreover, nicotine substitution itself can lead to addiction and isolated nicotine indulgence is also hazardous to health. Dependences on nicotine chewing gum are described in the literature, even with people who have never smoked. On the whole, success with nicotine substitution is limited.

There are an increasing number of drugs available for treating withdrawal of smoking, which are not based on nicotine replacement therapy. At present, vareniclin, a partial nicotine agonist, is considered successful and has been authorized for this purpose (Champix® in EU since December 2006; Chantix® in the USA). The compound occupies the receptor (the a4b2-nicotinergic acetylcholine receptors) and initially has the same effect—as desired—as nicotine. The smoker's attempt to enhance the effect of varenicline (Chantix®) by additional cigarette indulgence fails because varenicline keeps the nicotine receptor occupied and, thus, the pleasant effect of smoking is reduced. Within one year, however, three quarters of varenicline patients relapse and begin smoking. Furthermore, the therapy involves side effects, including nausea, headache, sleeplessness, vomiting, flatulence, insomnia, abnormal dreams and dysgeusia (gustatory disorder). Severe neuropsychiatric symptoms seem to occur rarely, however, they are significant since they are dangerous (FDA information February 2008). Further, since myocardial infarction was observed in connection with varenicline, the product information was up-dated following the authority's initiative according to the marketing authorization for medicinal products in Europe, although it is still unclear to what extent these complications were causally triggered by varenicline.

The antidepressant bupropion (Zyban®) is also an authorized medicament for the withdrawal of smoking. Bupropion can double the likelihood of a success in stopping a smoking habit. The active agent bupropion makes the reuptake of norepinephrine, serotonine and dopamine in the brain more difficult. It is not known why bupropion helps with the withdrawal of smoking but it is assumed that there is a connection with noradrenergic and/or dopaminergic mechanisms. This therapy also has very severe side effects including allergies, eczemas, itching, local oedemas, depression, sleeplessness, enhancement of delusions, hallucination orpsychoses, and convulsions. In general, bupropion is only recommended for healthy smokers.

According to an overview by Cochrane Collaboration, the hypertension medicament clonidine (Catapresan®), which is also used for withdrawal therapy of "hard" drugs, and the antidepressant nortriptyline are effective in treating smoking withdrawal. However, both of these medications are hardly prescribed due to their side effects.

The psychological dependence of a smoking habit is therapeutically approached by using nicotine-free herbal cigarettes (Arco Pharmaceuticals). Through their use, the person in withdrawal learns that smoking itself is not an addictive action. People who have stopped smoking by means of this method report that there is no fear of loss; they do not miss cigarettes. However, there are no studies regarding the effectiveness of this method.

The effect of immunization directed against nicotine is still being examined. Nicotine-specific antibodies are produced, which intercept nicotine, preventing nicotine from reaching the brain and triggering the addictive actions and actions that satisfy the addiction.

The available methods and medications for smoking withdrawal are largely unsatisfying. Many medications can only be used with carefully selected patients and, partly, cause dangerous side effects. Thus, their effectiveness is extremely limited. Moreover, they demand great self-motivation from smokers such that they can resist the desire for cigarettes. Their use is only justified because smoking causes increased morbidity and mortality.

Not all smokers suffer addiction in the same way. Dependence increases with increasing length of nicotine abuse and with the number of cigarettes consumed daily. The extent of dependence can be determined by tests known in the art. One such test, the Fagerström Test for Nicotine dependence (FTND), is a method for determining smokers' physical nicotine dependence. In detail, it states nicotine-relevant addiction criteria in question and answer form. For example, how quickly someone takes their first cigarette after getting up in the morning and how important this cigarette is, how many cigarettes are smoked daily and whether the smoker complies when smoking is prohibited (see, e.g., Heatherton, T. F. et al. Brit. J. Addict 86 (1991), 1119-1127).

One question of the Fagerström Test "Do you smoke even if you are ill and have to stay in bed?" reflects the fact that with illness, in particular with viral flu-triggering infections, which clearly affect the sense of well-being, smokers often have considerably less desire for nicotine. It is known that with poor general health, the desire for nicotine is reduced. Smokers who are addicted to a lesser degree (fewer than 20 cigarettes a day) are those who no longer have a need to smoke when suffering from colds or other illnesses. In cases of severe influenza, only extremely addicted smokers still have a need to smoke cigarettes. However, even in those cases, in general, there is a clear reduction in the need.

II. Food Addiction

Food addicts exhibit altered brain mechanisms, similar to drug addicts, and experience similar withdrawal symptoms (Davis et al., Appetite (2009) 53:1-8).

Overweight and malnutrition are a widespread cause for various diseases, increased morbidity and extremely high health-care costs. According to the World Health Organization (WHO), overweight is caused by a tendency to consume high-fat food. Like other health organizations, WHO recommends fat consumption corresponding to 30% of nutritional energy. Experts recommend reducing the consumption of saturated fatty acids to successfully control weight and prevent sequelae such as diabetes mellitus and other metabolic diseases, which increase coronary risk. In the Federal Republic of Germany, about 40 percent of the inhabitants are overweight, (BMI>25). In general, overweight people consume more fat than people of normal weight. Fat has a very high caloric value (1 gram fat provides more than twice the calories compared to 1 gram carbohydrates) and plays a major role in the development of overweight. The regulation of hunger and feeling of satiety respond better to carbohydrates than to fat. In the case of adipositas, as well as in the case of eating disorders such as bulimia and binge eating, the regulatory mechanisms of appetite, hunger and feeling of satiety does not work at all or works insufficiently. The causes of this disorder are not yet known in detail and various factors may be involved.

Several methods are known in the prior art that attempt to curb excess food consumption. In severe cases, in order to restrict the food consumption by food addicts, a gastric band or balloon can be introduced into the stomach. This limits the amount of food that can be eaten at meals by causing a sensation of fullness and mechanical satiety stimuli. Some non-prescription drugs are thought to have a similar effect. These drugs are swallowed as capsules and disintegrate in the stomach, swelling like a sponge. There are also commercially available anorectics acting on the hunger center or the satiety center in the hypothalamus. Usually this effect is caused by enhancing the production of noradrenaline, dopamine and serotonine in the brain. The activation of the serotonine receptor sub-type 2C (5-HT2C) is also considered as a possible mechanism of the anorectic effect of standard appetite suppressants. The inhibition of the cannabinoid receptor CB1 also has a significant appetite suppressing effect. Studies have shown that the effect of these preparations on the brain considerably declines after some weeks. In the 1960s, the appetite suppressants used were primarily amphetamine derivatives, which act on the central nervous system. The majority of these preparations are no longer authorized for marketing since when taken over a longer period of time, they lead to dependence and may cause severe side effects.

Xenical (orlistat), a pharmaceutical composition authorized for the European market is not an anorectic but instead acts directly on the digestion of fat. Orlistat inhibits gastrointestinal lipases (enzymes that break down fats). When these enzymes are inhibited, they are no longer capable of breaking down specific fats contained in food such that approximately 30% of the fats consumed with food passes undigested through the intestine. These fats are not able to be used or converted into fat tissue, which supports loss of weight. The most frequent side effects of Xenical (observed with more than 1 of 10 patients) are influenza, hypoglycaemia (low blood glucose level), headache, infections of the upper respiratory system (colds), abdominal pain and multiple problems in connection with bowel movement.

It is known that virus infections (e.g. influenza) cause spontaneous loss of appetite which results, without effort of will but rather in a spontaneous manner, in reduced food consumption. However, the infection of patients with a virus (e.g. influenza) is not an acceptable alternative treatment for food addiction.

III. Cytokines (Immune Modulators)

The cells of the immune system that are responsible for blocking bacteria, viruses, fungi and other deleterious effects within an organism "communicate" chemically via soluble endogenous messenger substances. The cells produce a great number of such "messenger substances" which are released at all sites where an immune reaction occurs and which function as a signal for other cells. In this way the cells are activated to function. Endogenous substances having such function are referred to as cell hormones or cytokines. A cytokine is defined as a small protein released by cells that has a specific effect on the interactions between cells, on communications between cells or on the behavior of cells. The cytokines include the interleukins, lymphokines and cell signal molecules, such as tumor necrosis factor and the interferons, which trigger inflammation and respond to infections.

Cytokines have been classified as lymphokines, interleukins, and chemokines, based on their presumed function, cell of secretion or target of action. Today it is know that cytokines are characterized by considerable redundancy and pleiotropism. Many cytokines share similar functions. Cytokines are substances that are secreted by specific cells of the immune system which carry signals locally between cells, and thus have an effect on other cells. They are a category of signaling molecules that are used extensively in cellular communication. They are proteins, peptides, or glycoproteins.

Interferons (IFNs) are a large family of multifunctional secreted proteins involved in antiviral defense, cell growth regulation and immune activation (reviewed in Vilcek S, and Sen G. Interferons and other cytokines, Virology, Editors Fields, Knipe, Howley, Lippincott Raven Philadelphia, 375-399). The biomodulatory activities pertinent to this group of cytokines have been extensively exploited at the clinical level, and are used in therapy for many viral diseases, hematological malignancies and multiple sclerosis. Viral infection induces transcription of multiple IFN genes; Type I IFNs (e.g., IFN-α or IFN-β) are produced by a variety of cell types, while Type II IFN (e.g., IFN-γ) is produced by T-cells and natural killer (NK) cells. Newly synthesized IFNs interact with neighbouring cells through cell surface receptors, resulting in the rapid and efficient synthesis of over 30 new cellular proteins through the activation of the JAK-STAT family of cellular transcription factors. These events represent the means by which IFNs induce the antiviral state that constitutes the primary host defense in innate immunity. Among the many virus and IFN-inducible proteins are a growing family of transcription factors, the Interferon Regulatory Factors (IRFs). IRF-1 and IRF-2 are the best characterized members of this family, originally identified by studies of the transcriptional regulation of the human IFN-β gene.

Systemic application of Type I interferons are of special concern because Type I interferons have been shown to modulate the opioid, serotonin, dopamine and glutamate neurotransmitter system in a dangerous way and it is generally recommended that they should be administered with caution because of the increased risk of severe life threatening psychiatric side effects. Psychiatric symptoms, conceptual disorganization, neurological deficits, cortical blindness, coma and, rarely, death have been reported, especially in elderly patients, following intramuscular or intravenous administration, at higher doses of frequent injections of IFN-alpha and in primary renal cell carcinoma (Merimsky, O. and Chaitchik, S. Anticancer drugs 3:5667-70 (1992)). The duration of the treatment was not strongly related to neurotoxicity.

Cytokines mediate the communication between leucocytes and also between other cells involved in immune reactions (e.g. macrophages). Interleukins are peptide hormones belonging to the group of cytokines.

Interleukin-2 is the most important signal for a helper T-cell. After being stimulated, the helper T-cell releases interleukin-2. This signal essentially has an autocrine effect on the helper T-cell itself. An intracellular signal cascade causes activation and clonal division of the T-cells. Once they have recognized their antigen, they replicate. Thus, this interleukin is one of the growth factors. Apart from acting on autocrine cell activation, interleukin-2 also acts on B-lymphocytes and natural killer cells with a similar effect. Interleukin-2 also acts on cell functions (for example: killer activity with respect to "foreign" cells or degenerated cancer cells). Since 1983 it has been possible to produce interleukin-2 with recombinant DNA technology methods and thus, it is available in sufficient amounts for scientific studies and clinical use. Consequently, interleukin-2 is one of the best-analyzed cytokines and is of great therapeutic significance. The therapeutic action on the immune response (the defense of the organism) is referred to as immune therapy or immune modulation. This type of therapy aims at using endogenous defense mechanisms for the treatment of diseases.

At present, cytokines such as interleukins and interferons are used primarily for the treatment of various life-threatening tumor diseases. For example, interleukin-2 (IL-2) and/or interferon-alpha (INF-α) are used in the treatment of kidney cancer, melanoma and severe infectious diseases (e.g., IFN-α in the treatment of hepatitis and IL-2 in the treatment of AIDS). The cytokines cause proliferation and multiple activation of immune cells, finally resulting, inter alia, in killer activity of immune cells directed against tumor cells. The therapies are essentially administered in the form of systemic (e.g. intravenous or intramuscular) administration, which is well-known to cause undesired side effects that are generally referred to as "flu-like" and include fever, chills, diarrhea, increased heart beat, reduced blood pressure, loss of appetite, nausea, and vomiting. These side effects may be severe, particularly in patients suffering from concomitant diseases, and can even result in death caused for example by myocardial infarction. These side-effects are accepted since the diseases treated with immune modulators are life-threatening (kidney cancer, melanoma, aids, hepatitis, etc.) and the cytokines can successfully treat these diseases.

Various methods have been developed, many of which are not authorized for marketing, for administering cytokines to treat severe diseases more tolerably and to reduce the life-threatening side-effects. Modifications of the dosage schemes, co-medication and, particularly, changes in the administration forms, e.g. systemic administration (subcutaneous, intravenous, intramuscular) into local application methods (inhalation, nasal, oral, buccal, and intravesical administration and others) maintain immunological efficacy and reduce the side effects (see, e.g. Thipphawong, J. Advanced Drug Delivery Reviews (2006) 58:1089-1105). Local administration of cytokines are considered to be "more physiological" since they cause release of high doses of signal molecules at the site of the reaction without causing general systemic Side effects. Contrary to systemic administration via injections/syringes or infusion, inhalational administration, especially in the case of lung metastases and lung tumors, does not cause flu-like symptoms and is comparatively well-tolerated with side effects limited to moderate impairment in the pulmonary region (e.g., dose-dependent cough, slight reduction of pulmonary function). Apart from the known inhalation application of interleukin-2 for the treatment of malignant tumors in the pulmonary region, cytokines are also administered as immune modulators by means of subcutaneous low-dose injections, which in low dose schedules are also well-tolerated. These low dose subcutaneous schedules are, however, very limited as to the anti-tumor effect and, apparently, are not able to cause the desired immune modulation to the extent required. The different application methods (e.g. via inhalation and syringe/injection) and also the different immune hormones (e.g. interleukin-2 and interferon-alpha) are sometimes administered in combination in order to improve the treatment results. Exclusively local therapies as well as therapy forms administered in combination to enhance tolerance are immunologically active, as concomitant studies of hematological cells (as to proliferation, surface activation markers) have proven. Yet, local administration of cytokines has failed to meet expectations. It has been found that local administration of cytokines cannot effectively treat the whole body of the patient. For example, lung metastases can be effectively treated by inhalation of cytokines but metastases in other locations are not effectively treated. Thus, the medical community currently recommends systemic administration of cytokines for disease treatment, at least in those who can tolerate systemic side effects.

It has further been suggested that oral and buccal administration of interferons and other cytokines may induce local and systemic effects while also being well-tolerated. Interferon-alpha applied in the oral cavity affects the oral mucosa and it is possible that these effects are even protected against blocking antibodies that are present in the blood stream (Georgiades et al. Biotherapy (1996) 8:205-212). However, further studies would be required to determine if this route of administration is effective for disease treatment.

Considering the severe heath issues associated with addiction, including addiction to nicotine, alcohol and/or sex, and addiction to food and/or overindulgence in food and the small success rate of current treatments for these addictions, new treatments for these addictions are highly desirable. Thus, the technical problem underlying the present invention is the provision of a treatment for dependent and/or addictive behavior, in particular addiction and/or dependency to nicotine, addiction to food, alcohol addiction and/or sex addiction.

The present invention relates to a cytokine for use in the treatment and/or control of dependent and/or addictive behavior, in particular addiction and/or dependency to nicotine, food addiction, alcohol addiction and/or sex addiction. The present invention also relates to treatment and/or control of withdrawal and/or symptoms of withdrawal from an addiction, in particular nicotine addiction, food addiction, alcohol addiction and/or sex addiction. The present invention further relates to the induction of loss of interest or aversion to the addictive substance or behavior, such as nicotine, over-indulgence in high-calorie, high-fat foods, and to other behaviors or addictions that are hazardous to the health.

Accordingly, the invention herein described provides a cytokine for use in treating an addiction.

In an alternate embodiment, a method for treating an addiction in a patient in need thereof, comprising administering a therapeutically effective amount of a cytokine is provided.

In a further embodiment, the addiction is nicotine addiction, alcohol addiction, sex addiction or food addiction.

In a further embodiment, the cytokine is stabilized.

In an alternate embodiment, the cytokine is substantially pure.

In a further embodiment, the cytokine is interleukin or interferon.

In a further embodiment, the interferon is a Type I interferon or Type II interferon.

In a further embodiment, the interleukin is interleukin-1, interleukin-2, interleukin-8, interleukin-12 or interleukin-18.

In a further embodiment, the cytokine is a Type II interferon, which is interferon-gamma.

In a further embodiment, the cytokine is a Type I interferon, which is interferon-alpha and interferon-beta.

In a further embodiment, the nicotine addiction is to a tobacco product.

In a further embodiment, the cytokine is administered by local administration.

In a further embodiment, the local administration of the cytokine is by mucosal administration.

In a further embodiment, the mucosal administration of the cytokine is administration onto the respiratory tract, administration onto the gastrointestinal tract, intravesical administration or intravaginal administration.

In a further embodiment, the administration of the cytokine onto the respiratory tract is nasal administration.

In a further embodiment, the administration of the cytokine onto the gastrointestinal tract is of oral administration, buccal administration or rectal administration.

In a further embodiment, the cytokine is administered by inhalation.

In a further embodiment, the cytokine is administered at a dose in the range of 0.0001 MIU to 54 MIU per day.

In a further embodiment, the cytokine is administered at a dose in the range of 0.0001 MIU to 36 MIU per day.

In a further embodiment, the cytokine is administered at a dose in the range of 0.1 MIU to 18 MIU per day.

In a further embodiment, the cytokine is administered at a dose in the range of 1 MIU to 9 MIU per day.

In a further embodiment, the cytokine is administered at a dose in the range of 10 ng to 3.3 mg per day.

In a further embodiment, the cytokine is a mixture of two substantially pure cytokines.

In a further embodiment, the cytokine is administered as a daily dose that is divided into 2 or more portions per day.

In a further embodiment, the cytokine is administered as a daily dose that is divided into from 1 to 10 portions per day.

In a further embodiment, the cytokine is administered at a dose to significantly increase nitric oxide in air exhaled by the patient.

In a further embodiment, the cytokine is administered at a dose to significantly increase the number of eosinophil granulocytes in the bronchoalveolar system.

In a further embodiment, the cytokine is administered at a dose to significantly increase the number of interleukin-2 receptor positive cells in the bronchoalveolar system.

In a further embodiment, the cytokine is administered in combination with one or more flavoring agents.

In the context of this invention, cytokines include cytokines classified as T helper cytokines, including T helper 1 ($T_h1$) cytokines, T helper 2 ($T_h2$) cytokines, T helper 17 ($T_h17$) cytokines and follicular helper T cells ($T_{fh}$). T helper 1 cytokines are involved in the cell-mediated immune and inflammatory response. Examples of $T_h1$ cytokines for use in this invention include interleukin-2 (IL-2), interferon-gamma (Interferon-γ or IFN-γ), tumor-necrosis-factor alpha (TNF-α) and beta (TNF-β), interleukin-12 (IL-12), interleukin-18 (IL-18), and follicular helper T cells ($T_{fh}$) including interleukin-21 (IL-21), interleukin-6 (IL-6) and interleukin-10 (IL-10). T helper 2 cytokines mediate the humoral immune responses, such as antibody production and allergic response. Examples of $T_h2$ cytokines for use in this invention include interleukin-4 (IL-4), interleukin-5 (IL-5), interleukin-13 (IL-13), interleukin-18 (IL-18), interleukin-25 (IL-25) and, interleukin-33 (IL-33). Examples of $T_h17$ cytokines for use in this invention include interleukin17 (IL-17), interleukin-23 and lymphocyte growth factors including interleukin-7 (IL-7) and interleukin-15 (IL-15) and pro- and anti-inflammatory and proliferation stimulating cytokines including interleukin-1

(IL-1), interleukin-1α, interleukin-1β, interleukin-3 (IL-3), interleukin-9 (IL-9), interleukin-11 (IL-11), interleukin-13 (IL-13), interleukin-14 (IL-14), interleukin-15 (IL-15), interleukin-16 (IL-16), interleukin-19 (IL-19), interleukin-20 (IL-20), interleukin-21 (IL-21), interleukin-22 (IL-22), interleukin-23 (IL-23), interleukin-24 (IL-24), interleukin-25 (IL-25), interleukin-26 (IL-26), interleukin-27 (IL-27), interleukin-28 (IL-28), interleukin-29 (IL-29), interleukin-30 (IL-30), interleukin-31 (IL-31), interleukin-32 (IL-32), interleukin-33 (IL-33), interleukin-34 (IL-34), interleukin-35 (IL-35), and pro- and anti-inflammatory colony-stimulating, factors.

Further, in the context of this invention, included are cytokines that induce nitric oxide (NO) increases. Examples of cytokines that induce NO increases include interleukin-1 (IL-1), interleukin-1β (IL-1β), tumor-necrosis factor-α (TNF-α), interleukin-2 (IL-2), and interferon-γ (INF-γ). Additional cytokines useful in the context of this invention include interleukin-8 (IL-8), interferon-α (INF-α) and interleukin-β (INF-β). Preferred cytokines of this invention include interferon-γ (INF-γ), interferon-α (INF-α) and interleukin-2 (IL-2). Even more preferred cytokines of this invention include interferon-γ (INF-γ) and interleukin-2 (IL-2).

In a further embodiment, the cytokine of the treatments disclosed herein are stabilized. Methods of cytokine stabilization are well-known in the art. Any method of stabilization that does not significantly decrease the biological activity of the cytokine and is compatible with the mode of administration, is suitable for the treatments discloses herein. Examples of stabilized cytokines include methods described in EP-A2 0 251 001, Ruiz L et. al., PDA J Pharm Sci Technol. (2006) January-February; 60 (1):72-8, or Hawe, A. (Dissertation, 2006) "Studies on stable formulations for a hydrophobic cytokine".

Poor solubility of cytokines and the tendency of these hydrophobic proteins to adsorb on surfaces are the major challenges. The hydrophobicity of these proteins is further increased when they are recombinantly produced in *Escherichia coli* (*E. coli*) as host cells, as glycosylation is not possible in *E. coli*: Human Serum Albumin (RSA) is frequently used as an excipient and HSA-free formulations for hydrophobic proteins are described in patents and literature. In its function as cryo- and lyoprotector, HSA can be replaced by sugars, sugar alcohols or amino acids. By adjusting the formulation pH and ionic strength, protein solubility can be optimized and adsorption reduced. Cyclodextrins, which are cyclic oligosaccharides composed of six to eight dextrose units, can be used to enhance the solubility of proteins.

Protein adsorption is most effectively addressed by the addition of surfactants and can be solved by the use of container materials which are less prone to adsorption e.g. glass type I. Adsorption of three model proteins (hen egg white lysozyme, bovine serum albumin and ribonuclease A type IIA) onto different surfaces was reduced up to 30% by increasing the sugar concentrations, with trisaccharides being more effective than disaccharides and monosaccharides (Wendorf, J. R. et al. Biotech. Bioeng. (2004) 87:565-573). The addition of an excess of Human Serum Albumin to the active protein is another common approach to reduce the loss of the active protein due to adsorption. HSA inhibits protein adsorption and stabilizes different hydrophobic cytokines (e.g., interleukins such as IL-1aα, IL-1β, IL-2, IL-3, macrophage colony-stimulating factor) during lyophilization (see Dawson, P. J. Dev. Biol. Stand. (1992) 74:273-82 and EP-A2 0 251 001). The addition of 0.1% HSA to formulations of TGF-α can prevent absorption on polyethylene, polystyrene and glass tubes measured after 24 hours (Jørgensen et al., Scan. J. Clin. Lab. Invest. (1999) 59:191-198).

A combination of HSA and mannitol as excipients for the stabilization of proteins is commonly described in literature and patents, especially for hydrophobic proteins like interleukins and interferons (see, e.g., U.S. Pat. No. 4,992,271, EP-A2 0 942 284, and WO 1995/031479). Mannitol is a standard excipient for lyophilization due to its excellent cake forming qualities.

Buffers useful for formulating include, but not limited to, MES, HEPES, citrate, lactate, acetate, and amino acid buffers known in the art.

Sugars useful for preparing include, but are not limited to, glucose, sucrose, trehalose, lactose, maltose, raffinose, stachyose, maltodextrins, cyclodextrins, sugar polymers such as dextrans and their derivatives, ficoll, and starch.

The protein compounds useful in the formulations of the present invention can be used in the form of a salt, preferably a pharmaceutically acceptable salt. Useful salts are known to those skilled in the art and include salts with inorganic acids, organic acids, inorganic bases, or organic bases.

In a further embodiment, the cytokine of the treatments disclosed herein are substantially pure. Methods of producing a cytokine in substantially pure form include methods well known in the art such as those based on recombinant DNA technology (Maniatis, Molecular Cloning: A Laboratory Manual (2001)). In the context of the invention herein disclosed, more than one substantially pure cytokine may be administered as a combination, simultaneously, separately or sequentially according to the treatments herein described.

In a further embodiment, cytokine mixtures, in particular those containing significant amounts of interleukin-2, such as Leukocyte Interleukin Injection or Multikine® (described in WO 2006/015137) may be administered according to the treatments described herein.

Without being bound by theory, it is believed that the increases in NO induced by the cytokines of the present invention is related to the development of the loss of interest or aversion to use of nicotine products or over-indulgence in high-fat, high-calorie food. Thus the treatments described herein are useful in altering the psychological and/or physiological addiction of the nicotine addict or food addict.

Accordingly, the present invention provides a cytokine for use in treating an addiction.

In a further embodiment, the invention provides a method for treating an addiction in a patient in need thereof, comprising administering a therapeutically effective amount of a cytokine.

In a further embodiment, the invention provides the use of a cytokine for the manufacture of a pharmaceutical composition for the treatment of an addiction.

In a further embodiment, the addiction is selected from the group consisting of nicotine addiction, alcohol addiction, sex addiction and food addiction. In a further alternate embodiment, the nicotine addiction is to a tobacco product.

In an alternate embodiment, the cytokine is stabilized. In a further alternate embodiment, the cytokine is substantially pure.

In a further embodiment, the cytokine is selected from the group consisting of interleukin and interferon. Preferably, when the cytokine is an interleukin, the interleukin is selected from the group consisting of interleukin-1, interleukin-2, interleukin-8, interleukin-12 or interleukin-18. Preferably, when the cytokine is an interferon, the interferon is a Type I interferon or a Type II interferon, A preferred Type II interferon is interferon-gamma. Preferred Type I interferons include interferon-alpha and interferon-beta.

In a further embodiment, the cytokine is administered by local administration. In a preferred further embodiment, the local administration is selected from the group consisting of mucosal administration such as intrapulmonary administration, administration into the respiratory tract, including nasal administration, intragastrointestinal administration, including oral, buccal and rectal administration, intravesical administration and intravaginal administration. In a more preferred embodiment, the cytokine is administered by inhalation.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, general health, sex, diet, mode and time of administration, rate of excretion, drug combination, the severity of the particular addiction, and the individual undergoing therapy. Additionally, the dose my be adjusted as the treatment according to the present invention progresses. The precise dose and route of administration will ultimately be at the discretion of the attendant physician.

A proposed, yet non-limiting dose of the cytokine according to the present invention for administration to a human is at a dose in the range of 100 international units (or 0.0001 MIU) to 54 million international units (MIU) per day, preferably 0.0001 MIU to 36 MIU per day, more preferably 0.1 to 30 MIU per day, even more preferably 0.1 to 18 MIU and most preferably 05 to 9 MIU of the cytokine per day. In a further embodiment, the cytokine is administered at a dose in the range of 1 MIU to 9 MIU per day. This dosing regiment is particularly useful for cytokines such as interleukin-2 and interferon-alpha. However, the dose may be adjusted to achieve the therapeutic effect for the cytokines herein described.

A proposed yet non-limiting dose of recombinant human tumor necrosis factor alpha (rhTNF-α) for a single daily inhalation may be 60 ng in 1% human albumin-phosphate buffered saline. Similar doses have been reported to increase exhaled nitric oxide and airway responsiveness and sputum inflammatory cells (Thomas et al. Thorax (2002) 57, 774-778) Immunomodulation has been observed by daily doses of interleukin-2 in the range of 0.05 mg-2 mg or of tumor necrosis factor alpha (TNF-α) at a dose of 60 ng. Doses of cytokines may need to be adjusted and can be monitored using functional parameters like nitric oxide measurements and monitoring of peak flow measurements.

For interferon gamma doses of 250-1,000 μg were inhaled as an aerosol once daily for 3 days and described to be effective (Jaffe, The Journal of Clinical Investigation, Inc. (1991) Volume 88 (July), 297-302).

For the available interleukin-2 preparations doses to be used are known and described for other medical indications. However, these described doses may also be adjusted for example when cytokine fragments or prodrugs are used, which induce comparable immune modulation but have a different weight or a different receptor binding.

Doses described herein are descriptive and other dosing schedules inducing similar immunomodulation for other cytokines can be determined using the parameters herein described. Functional parameters may be useful to detect immunomodulation that is capable of influencing drug addiction.

In a further embodiment, the cytokine is administered at a dose effective to significantly increase nitric oxide in the exhaled air.

In a still further embodiment, the cytokine is administered at a dose effective to significantly increase the number of eosinophil granulocytes in the bronchoalveolar system.

In a further embodiment, the cytokine is administered at a dose effective to significantly increase the number of interleukin-2 receptor positive cells in the bronchoalveolar system.

In a further embodiment, the cytokine is administered at a dose effective to significantly increase nitric oxide, the eosinophil granulocytes or the interleukin-2 receptor positive cells in the mucosa.

Because prodrugs are known to enhance numerous desirable qualities of pharmaceuticals (solubility, bioavailability, manufacturing etc.) the scope of the present invention further embraces pharmaceutically acceptable prodrugs of the cytokines as defined and described herein. Such pharmaceutically acceptable prodrugs are derivatives of the respective cytokines which have chemically or metabolically cleavable groups and become, by solvolysis or under physiological conditions, the cytokines as defined and described herein, which are pharmaceutically active in vivo. Prodrugs of the cytokines as defined and described herein may be formed in a conventional manner with a functional group of said compounds such as with an amino, hydroxy or carboxy group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985).

In an alternate embodiment, the cytokine is a mixture of two substantially pure cytokines.

In a further alternate embodiment the cytokine is a mixture of cytokines each of which is proportionally present in an amount that mimics the excretion by a healthy immune system. An example of such a mixture includes, but is not limited to, Multikine®.

In an alternate embodiment, the daily dose of the cytokine is divided for administration into 2 or more portions per day. In a further embodiment, the daily dose is divided for administered into from 1 to 10 portions per day. In a further embodiment, the daily dose is divided for administered into 1 to 5 portions per day.

The term "treatment" of an addiction as used herein is well known in the art. The term "treatment" includes discontinuation of use, decrease of use, prevention of relapse, reduction in severity of use, reduction in desire and/or cravings, reduction in withdrawal symptoms, reduction in desire to use addictive products, increase is aversion to the addictive products, and loss of interest in the addictive product. In the context of the invention herein described, the term "treatment" may also include an increase in the desire for nutritious healthy foods.

As used herein, the term "addiction" shall include abuse, dependency, craving, including, but not limited to post-deprivation craving, post-withdrawal craving, relapse craving, withdrawal, and related disorders.

As used herein, the term "control" in the context of the treatment of an addiction is well known in the art. The term "control" includes an ability to withstand cravings, to exercise restraint with regard to the addiction, and to resist temptation in the presence of the addictive substance or behavior.

As used herein, the term "substantially pure" in the context of the cytokines for use in the invention described herein means that the cytokine is synthesized or obtained without substantial contamination from other cytokines. In the context of the cytokines for use in the invention herein described, medical grade cytokine or cytokine of purity as would be accepted by the Federal Drug Administration or the European Medicines Agency are considered "substantially pure".

In the context of the invention herein described, local administration of cytokines does not lead to significant systemic absorption, systemic toxicity or systemic side effects. As used herein, the terms such as "no measurable cytokine in the blood", administration of cytokines "does not result in measurable systemic absorption, systemic therapeutic effects or systemic side effects" "absence of measurable systemic interleukin-2 blood levels", and "the cytokine is not measurably systemically absorbed" shall be understood to include minute measurable amounts of cytokine as a result of minor absorption. For example, at high doses it is expected that some percentage, generally 1% or less of the administered cytokine, may toe systemically absorbed. Even with lower doses of cytokine administered locally there may be some minor absorption. This would be expected as the cytokines are being administered to a biological system. However, insignificant systemic toxicities or systemic side effects would be expected to result from such minor absorption. Such minor absorption from local administration of cytokines is not expected to result in the systemic toxicities or side effects associated with systemic administration of cytokines.

The invention provides a solution to effectively influence nicotine dependence, misbehavior by excessive eating or abuse of high-fat, high-calorie food by immune modulation and the use of endogenous regulatory mechanisms caused thereby. The immune modulation with cytokines represents a completely new strategy for routine clinical therapy and prevention and provides important advantages in comparison to the methods available so far.

In contrast to conventional therapies and to the attempts of immunization with nicotine, the present form of therapy does not aim at keeping the dependence-causing substance away from the target or at replacing the dependence-causing substance. The lack of desire for the dependence-causing substance is a secondary phenomenon of cytokine-based immune modulation which, surprisingly, occurs even when optimized application methods are used that do not result in systemic absorption and do not cause flu-like fever, which involves deleterious effects on the patients health, but act mainly or exclusively locally. While withdrawal symptoms and intense desire for the dependence causing substance are a consistently recurring problem of conventional therapies, immune modulation with cytokines, and, even more surprising, local immune modulation, has the effect to reduce the desire as a natural secondary phenomenon, essentially without causing withdrawal symptoms.

Intravenous, intraarterial, intramuscular and subcutaneous administrations of cytokine(s) result in systemic intravenous availability, systemic therapeutic effects and are associated with systemic side effects and toxicities. Inhalation of cytokines does not result in measurable systemic absorption, systemic therapeutic effects or systemic side effects. This is different to a large variety of inhaled medications where inhalation may substitute for intravenous application, because of a rapid absorption through the alveolar membrane, which is very thin, consisting of alveolar epithelium and capillary endothelium only and covering an overall size of about 100 m$^2$.

However, topical administration like inhalation of cytokines according to previously described methods (see U.S. Pat. No. 5,780,012), safely prevents cytokines and in particular interleukin-2 from being absorbed into the capillary endothelium. The large majority of the administered cytokine stays at the site of topical application and induces immunomodulatory effects there. This prevents systemic toxicity and offers a chance to treat patients who would not be able or willing to tolerate systemic side effects. It is known from treating diseases like lung cancer or lung metastases by topical inhalation of interleukin-2, that systemic toxicities have been avoided and absorption into the vascular system was not at all or only detected in minimal amounts at very high doses. Therapeutic effect is limited to the local area of administration, e.g. inhalation of interleukin-2 controls lung metastases only but was ineffective to control more distant metastases like liver or brain metastases (2008 Renal Cell Cancer: Diagnosis and Therapy, Springer Editors De La Rosette, Sternberg, van Poppel, Immunotherapy Huland et al. 427-449).

With the therapies available so far, the control of the desire for nicotine, cigarettes, excessive food, high-fat, high-calorie food, alcohol or sex requires great will power. The treatment with cytokines reduces the need to rely on will power. In some cases, behavior modifications occurs spontaneously and without effort by the person concerned.

Natural influenza, and influenza caused by systemic administration of immune modulators such as the cytokines, including interleukin or interferon, causes severe typical flu-like side effects such as fever, diarrhea, chills, reduced blood pressure, increased heart beat and changes in the fluid equilibrium. These side effects may even be life-threatening. It has been observed that the need for nicotine or for food is significantly reduced, without any effort by the nicotine or food addict, while experiencing these symptoms. While the application of cytokines for the induction of severe febrile illness with the goal of inducing behavior modification is possible, it presents several risks. First, the significant toxicity of such a therapy, which provokes influenza-like symptoms through immune stimulation, can be justified only in rare cases, if in any. Second, the systemic application of high doses of cytokines is a major problem for every day administration, which would interfere with the goal of administration, e.g., behavior modification. Third, systemic toxicity and side effects cannot be tolerated for many weeks or months, tolerability for long-term systemic therapy is highly limited even in cancer patients and it cannot be expected to be better in patients with addictive behavior.

Various immune hormones are suitable for the induction of influenza-like symptoms, these are, in particular, the immune hormones interleukin-2, interleukin 12, and further interleukins and the interferons, including interferon-alpha, interferon-beta and interferon-gamma. Some of these cytokines are available as pharmaceutical compositions authorized for the treatment of severe diseases, including cancers such as renal cell carcinoma and melanoma. Even though the systemic administration of cytokine suppresses the desire for a cigarette with clearly addicted smokers, use of these medications as approved (systemic administration) is hardly justifiable considering the life-threatening side effects or side effects that confine the patient to bed. Only in very severe cases (e.g. extreme adipositas, significant damages caused by smoking such as loss of extremities or the like) could the known side effects of a systemic immune therapy be considered acceptable for the purpose of behavior modification. For example, hospitalized heroin addicts subjected to extended periods of heroin deprivation, which was reported to cause a loss of desire for heroin, were later systemically administered porcine spleen extracts containing mixtures of cytokines, which induced the expected flu-like symptoms (RU-C1 2 290 947). However, for the average addict severe side effects are daunting and preclude the application of this systemic administration.

It has been surprisingly found that during inhalation administration of cytokines, in particular interleukin-2, despite the absence of flu-like symptoms associated with the immune response, an aversion to cigarette smoking is induced spontaneously and that nicotine addicts significantly reduce or stop smoking without will power, as such, being necessary. This loss of desire is correlated with the duration of therapy and the dose administered. This loss of desire develops in the absence of measurable systemic interleukin-2 blood levels. It has also been surprisingly found that an effect on food intake, in particular, with respect to the desire for high-calorie, high-fat food is similarly reduced.

The use of a substance, in particular the local use of a substance, that is naturally produced by the body (immune hormone, cytokine) for the induction of an immunologic reaction, which suppresses the need for the addictive substance or behavior, represents a completely new therapeutic approach for the control of addictions, including nicotine addiction, addiction to excessive eating, alcohol addiction and/or sex addiction.

The local approach by inhalation administration is particularly advantageous since it has few side effects and is much better tolerated than a systemic therapy by injections (see, e.g. Thipphawong, J. Advanced Drug Delivery Reviews (2006) 58:1089-1105). It is particularly advantageous for smokers because it satisfies the psychological need to inhale something (referred to as additive addiction potential). This form of administration is a partial answer to behavior patterns practiced for many years until the first difficult phase of addiction is overcome.

In comparison to nicotine replacement therapy, administration of a cytokine is particularly advantageous since the mere replacement of nicotine may continue to support addiction and, thus, may impede long-term, complete withdrawal. In contrast to all nicotine-containing or nicotine-free medicaments supporting addiction therapy, the immunological stimulation by immune hormones uses an apparently naturally occurring mechanism to effectively suppress the need for nicotine.

As is surprisingly observed from local administration of cytokines, in particular with inhalation administration of interleukin-2, influenza-symptoms with fever and secondary reactions are not necessary in order to obtain an effect of behavior modification resulting in aversion to nicotine, food, alcohol and/or sex. In addition, other well-tolerated forms of immune modulation by cytokines, such as local immune stimulation in the respiratory system or the gastro-intestinal tract, surprisingly have the same effect. Similar to a febrile illness, but without the associated flu-like symptoms, the local immune stimulation induces an aversion to nicotine and high-fat, high-calorie food and the diet is changed spontaneously to light, hypo-calorie low-fat food, and the caloric uptake is reduced significantly. After few days, the inhalation of interleukin-2 results in a significantly reduced desire for nicotine and smoking, even complete abstinence, and in spontaneous restriction of eating behavior, in particular, avoidance of high-fat food without will power being necessary.

It is known that inhalation and other local administrations of interleukin and interferon represent a form of administration of immune hormones that, even when administered in high doses, will generally not lead to systemic toxicities because the cytokine is not measurably systemically absorbed, whereas the same doses administered via systemic injection induce significant side-effects. For example, with inhalation, these side effects are essentially restricted to the local application site, the lung. This administration does not involve confinement to bed, a distinct feeling of illness or clear symptoms of influenza. During immunological therapy with local administration of cytokines, it is possible to work and to fulfill one's social role (e.g., child care, everyday duties). Some patients do not experience any restrictions, while other patients experience only a cough and reduced lung function, mostly of a moderate nature. Surprisingly, the smoker's need for nicotine is significantly reduced or even no longer exists when cytokines are applied locally. The treatment is thus applicable to a large group of patients that should not suffer severe side effects.

The treatments included herein show that it is possible to induce the natural effect of a febrile illness, which causes an aversion to nicotine, excessive food and other high-fat, high-calorie addictive substances, artificially by medication via immune stimulating pharmaceutical compositions (immune modulation via endogenous immune hormone) without the necessity of causing severe side effects and even without the necessity of inducing potentially toxic systemic blood levels of cytokines. The treatments included herein show that this new approach is successful due to the use of well-tolerated administration schemes and that this method of body regulation is well suited to effectively modify behavior, including nicotine dependence, excess eating, high-fat, high-calorie food abuse, alcohol addiction, and/or sex addiction in a justifiable manner while maintaining a daily routine.

Dosage and dosage intervals for the immune hormones may be adjusted to maintain reasonable quality of life while ensuring patient safety. The dosage and dosage intervals may be adjusted to achieve the desired local immune modulation. The local immune modulation may be measured by tests known in the art. For example, the inflammatory reaction, which causes the behavior modification with respect to smoking, excessive eating and other dependent behaviors and/or consumption misbehavior, can be assessed based on typical parameters such as nitric oxide (NO) increases, proliferation and activation of lymphocytes and other immune cells and proliferation as well as activation of eosinophils. The use of a personal peak flow meter helps to frequently assess lung function during cytokine therapy and ensures an adequate balance between control of craving and impairment of lung function.

A proposed, yet non-limiting dose of the cytokines according to the present invention for administration to a human is at a dose in the range of 100 international units (or 0.0001 MIU) to 54 million international units (MIU) per day, preferably 0.0001 MIU to 36 MIU per day, more preferably 0.1 to 30 MIU per day, even more preferably 0.1 to 18 MIU and most preferably 0.5 to 9 MIU of the cytokine per day. Dosing may also be measured in a corresponding unit such as mg. It is well known that, for example, 18 MIU interleukin-2 corresponds to 1.1 mg interleukin.

In an alternative embodiment, a proposed, yet non-limiting dose of the cytokines according to the present invention for administration to a human may be between 10 ng (nanogramm) to 3.3 mg (milligram) per day.

The daily dose may be divided into several portions for administration throughout the day. In one embodiment of the invention, the daily dose is preferably divided for administration into 2 or more portions. In a preferred embodiment, the daily dose is divided for administration into from 1 to 10 portions pre day and even more preferably from 1 to 5 portions per day. It will be appreciated that it may be necessary to make routine variations to the dosage depending on the age, weight and health of the patient as well as the severity of the addiction being treated. The precise dose and route of administration will ultimately be at the discretion of the attendant physician.

In addition, the types of nebulizer may influence the amount of the required dose. Technically advanced nebulizers may reduce the loss of medication during the nebulisation procedure, during the inhalation procedure or by other means and therefore may require lower doses to achieve similar effects in patients compared to older models of nebulizers.

In a further embodiment of the invention disclosed herein, the inhalation administration typically consists of multiple daily inhalations, for example 1 to 10 and more preferably 1 to 5, for a total daily dose of 0.5 to 36 MIU cytokine. This dosing regimen is particularly useful for cytokines such as interleukin-2, interferon-alpha and interferon-gamma. The dose and therapy duration required for a successful immune modulation may be adjusted depending on the individual degree of addiction and/or prior effects on the immune system. The individual patient's desire for nicotine and food may also be taken into account in deciding on the dose and therapy duration. Throughout the therapy, the dose may be adapted according to the patient's need. For example, after the initial days or weeks of therapy, the initial daily dose may be increased or decreased, depending on the patient's need. The dosage may be modified by the number of breaths so that the dosage may be determined by the patient according to need.

Doses for the inhalational application of interleukin-2 have been described in patents and in the literature with respect to tumor diseases and infectious diseases. These doses represent guideline values that initial therapy may be based upon. The dose can be adapted according to the patient's immune status, nicotine or food dependence and other individual factors such as measurements of peak flow meter, nitric oxide, lung function and local lung immunomodulation. Inhalation of interleukin-2 induces a dose-dependent immunomodulation in the lung, which includes an increase in total cells activation markers, IL-5 production, and nitric oxide. Major side effects include cough and fatigue.

Using the methods described herein, further cytokines can be identified which exhibit the desired properties. The skilled person will be able to determine whether the cytokine induces the desired behavior modification, e.g. indifference towards food, aversion to nicotine. Further, the person skilled in the art who is familiar with therapy schemes for interleukin-2 and, in particular, inhalations schemes, may adapt doses and therapy schemes described herein to achieve the desired behavior modification and to avoid intolerable toxic side effects by using optimized application schedules with no measurable cytokine in the blood.

Normally, specific cytokines can be detected in the saliva of healthy subjects also in low concentrations (interleukin-1, interleukin-8). In contrast, in the lung of smokers, the natural occurrence of interleukin-8 is already significantly increased (Mio, T et al. Am. J. Resp. Crit. Care Med. (1990) 155:1770). Cytokines, which are present in addicts in increased concentrations, may be less suited to induce an aversion to the addictive substance or behavior. The examination as to this effect may be carried out by the person skilled in the art using standard techniques. So far, the exact mechanisms underlying the aversion to nicotine or high-fat food or other dependence-inducing substances or behavior, which is caused by immune modulation and which is observed in the practice of the treatments of the invention, are not clear. To the person skilled in the art who is familiar with the results obtained with local administration of cytokines, in particular interferon and interleukin-7, it will be technically feasible to rapidly test whether the cytokine provides the aversion or loss of interest as described herein. Preclinical tests in animals and clinical tests in a limited number of humans can provide a rapid proof of principle for each cytokine. For example, by using the cytokine by inhalation and measuring craving, immune modulation and lung function. In particular a correlation with time and dose and the loss of craving is a rapid and reliable system to measure the desired effect.

The use of immune modulating substances allows a new approach to addiction and/or withdrawal therapy based on a natural response that spontaneously induces behavior modifications and significantly supports them without strict discipline being required. One advantage is the loss of interest and aversion to nicotine and excessive food which is induced "spontaneously" by the new immune modulating strategy. The known treatments (e.g., nicotine replacement, nicotine receptor binding, antidepressants etc.) do not achieve this aim or are not satisfactory.

It is possible to combine the effects of conventional strategies and the treatments disclosed herein. The invention herein described is a well-tolerated therapy strategy based on natural mechanisms, which may be used alone, or optionally in combination with conventional treatments for addiction. The immunological modulation is a new method based on natural regulation for the control of appetite, control of the addictive behavior, and/or control of use of the addictive substance, and it can ensure long-term success of behavior modification applied alone or in combination with other measures.

Another advantage is that the inhalation of interleukin-2 causes very few side-effects and may be applied, for example, to patients suffering from organ malfunction (e.g. renal malfunction, obligatory dialysis). Under these circumstances, many medicaments (e.g. varenicline) cannot be applied.

Another advantage of the invention is the fact that the administration of cytokines as such does not cause addiction. Contrary to replacement therapies, this therapy will not lead to a different form of addiction. For example, nicotine containing chewing gums have addiction potential (Etter, J. F., BMC Public Health (2007) 7(147):159).

A further advantage of the invention is that it is not necessary that the therapy ends with a "tapering-off" phase, i.e. with a gradual reduction of the medicament used in therapy. On the contrary, after termination of the therapy, the immune modulation will be measurable for some days or weeks and, thus, its effect will outlast the duration of the therapy. If necessary, the addict may decide whether, when or if re-stimulation of aversion to the misbehavior is necessary by temporarily resuming the end phase of the therapy. Ending the inhalation therapy does not result in immediate withdrawal sensations or irritability. The desire for smoking will be reduced for some time after the end of the therapy, facilitating the maintenance of the desired behavior.

Furthermore, the administration of the cytokine by inhalation has the psychological advantage that smokers may satisfy their desire for the ritual of inhalation without responding to their addiction but the inhalation even counteracts the addiction. This applies also to re-stimulation of immune modulation after termination of treatment. For the satisfaction of this psychological need, methods such as the electronic cigarette, cigar or similar cigarette-like aerosol generators are particularly suitable for an application conceived for the properties of cytokines (e.g. temperature control).

The pharmaceutical compositions of the cytokines of the invention are preferably orally administered (e.g. as a tablet, capsule, pastilles, chewing gums, lozenges or as a solution such as gargle solutions or juice preparations), topically administered (e.g., intradermal, intranasal, ocular, buccal, and sublingual, including nasal sprays and nasal suspensions), by pulmonary administration (e.g., by inhalation or insufflation therapy using, e.g., an aerosol, e.g. through mouth or nose), or by gastrointestinal administration. More preferably, pharmaceutical formulations of the cytokines of the invention are administered on a mucosal membrane. More preferably, pharmaceutical formulations of the cytokines of the invention are administered via the respiratory or gastrointestinal tract. Most preferably, the pharmaceutical formulations of the invention are administered by inhalation.

The pharmaceutical compositions can be formulated by techniques known to the person skilled in the art, such as the techniques published in Remington's Pharmaceutical Sciences, 20th Edition. The pharmaceutical excipient(s) can be selected with regard to the intended route of administration and standard pharmaceutical practice. They can be formulated as solutions or in an undiluted form for inhalation using well known standard techniques.

For administration of the cytokines by inhalation, the pharmaceutical compositions may be formulated with sodium chloride, glucose solution, alcoholic solutions, buffer or other solubilizers, which are appropriate to be administered to a patient by means of inhalation, and have no unfavorable effect on the biological efficacy of immune hormones, and are suitable for aerosol generation using cytokines. Examples for suitable formulations are given in U.S. Pat. No. 5,780,012, can be found in the examples of stabilized cytokines as described in EP-A2 0 251 001 and in methods as described in Ruiz L et. al., PDA J Pharm Sci Technol. (2006) January-February; 60 (1):72-8 and in Hawe, A. "Studies on stable formulations for a hydrophobic cytokine" (Dissertation, 2006).

Further applications of cytokines in accordance with the treatments disclosed herein, which induce an immune modulation of the mucosa of the respiratory tract or the gastrointestinal tract causing a comparable proliferation of lymphocytes, eosinophils and/or causing in particular an increase in nitric oxide (NO), may comprise oral administration or intake of cytokines (in the form of tablets, pastilles, chewing gums, lozenges, gargle solutions, juice preparations, etc.), nasal intake of interleukin-2 (nasal spray, nasal suspension, etc.), and also local slow release forms or specific application forms such as nano- or micro-needle injection systems, which are introduced in the mucosa of the oral, buccal, nasal or pharyngeal regions.

Modifications of the dosage schemes, co-medication and, particularly, changes in the administration forms, e.g. systemic administration (subcutaneous, intravenous, intramuscular) into local application methods (inhalation, nasal, oral, buccal, and intravesical administration and others) maintain immunological efficacy and reduce the side effects. Local administration of cytokines are considered to be "more physiological" since they cause release of high doses of immune hormones at the site of the reaction without causing general systemic side effects or systemic cytokine levels in the blood.

The administration of cytokines by inhalation, orally or mucosally is adaptable to inclusion of a flavoring agents. Flavoring agents include natural and artificial flavors chosen from synthetic flavor oils and flavoring aromatics, and/or oils, oleo resins and extracts derived from plants, leaves, flowers, fruits and so forth, and combinations thereof. Further examples may include tobacco flavor, menthol, spearmint oil, cinnamon oil, peppermint oil, clove oil, bay oil, thyme oil, cedar leaf oil, oil of nutmeg, oil of sage, and oil of bitter almonds, artificial, natural or synthetic fruit flavors such as vanilla, chocolate, coffee, cocoa and citrus oil, including lemon, orange, grape, lime and grapefruit and fruit essences including apple, pear, peach, strawberry, raspberry, cherry, plum, pineapple, apricot and so forth. Flavoring agents also include flavor correctives such as mint and cigarette additives, such menthol, other ethereal oils, cocoa, ammonia, urea, fruit flavoring, licorice, maple syrup, molasses, honey, species, liquor, tea, coffee and natural and artificial sugars (see Increased Health Risk By Tobacco Product Additives—consequences for product regulation, Deutsches Krebsforschungszentrum (German Cancer Research Center) Heidelberg, 2005). The additives used in cigarettes may support the patient starting the treatments described herein. Having an essentially alkaline pH value, additives and flavoring agents cause a pleasant sensation upon deep inhalation. It has been reported that the inclusion of these types of additives prevent cough and irritation caused by inhalation and also provide the inhalation with a pleasant flavor.

For inhalation administration, any inhalation device that will not be deleterious to the biological activity of the immune modulating substances during nebulization may be suitable. Commercially available standard nebulizers or inhalation devices (e.g. ultrasonic nebulizers, pressure nebulizers, sprays, dry powder aerosol generators) are also suitable, provided that the bioactivity of the immune hormones is preserved. These devices are well-known in the literature. Preferably, the inhalation device does not restrict the patients mobility. In a preferred embodiment, the inhalation device is a small device resembling in form cigarettes, cigars or pipes (also known as e-cigarettes) are particularly suited to ensure the patient's mobility. It is also advantageous to provide these nebulizing devices with a temperature control and a feed back mechanism which controls the temperature during aerosol generation within a specific range so that the biological activity of the immune hormone is preserved. Whereas small nebulizer devices, e.g. those used in the therapy of cystic fibrosis, already comprise temperature control and feed back mechanisms. E-cigarettes, e-cigars or e-pipes for cytokine application according to the invention provided with a temperature control and a feed back mechanism are new. They are designed in such a way that aerosol generation, nebulization, etc. are carried out at temperatures or under conditions which ensure the stability of the cytokines such as IL-2, INF-alpha and INF-gamma. Thus, it is possible to use the smoking utensil like devices for the purpose of generation of cytokine aerosol. In one embodiment, a nebulizer with a capacity of 18 L/min, nebulizes a dose of 1 mL during 29 breathings and generates aerosol exclusively during 6 second-intervals during the inhalation phase has been proven to be functional. Another useful element of a nebulizer of this type is the integration of a collecting receptacle or filter for capturing the cytokine in the expiratory air of the patient. Although, with correct inhalation, the amount of cytokines contained in the expiratory air is low, this precautionary measure is reasonable for the safety and protection of the surroundings.

The optimum duration of the standard therapy covers the time until the patient is able to spontaneously forgo nicotine. The initial therapy may have a duration of 2 to 4 weeks, after which the standard therapy will either be stopped with the cytokine being only inhaled if necessary, e.g. when a need for nicotine is felt. The dose can be gradually reduced from e.g. 5 inhalations per day to 4, 3, 2 etc. per day, until the patient inhales the cytokine only in the case of need, e.g. in situations typically triggering the need, such as parties. The patient may not need cytokine inhalations for all days between these exceptional situations. In the course of the therapy, the patient determines the time needed for complete withdrawal by effectively suppressing the need for nicotine by inhalation of the cytokine as necessary. Heavy smokers may need more time and higher initial doses, more moderate smokers may succeed in shorter time and, on the whole, may need lower doses and shorter therapy periods. If necessary, even after gradual termination of the treatment, an application of multiple daily inhalations may be resumed over a period the patient considers to be necessary to control the desire for nicotine. In principle, the cigarettes the patient would smoke are replaced by the inhalation of the cytokine with the cytokine inhalations and/or doses being continuously reduced In exceptional cases, for example with heavy smokers, the withdrawal may be supported by a systemic injection therapy using low doses of the cytokine (in the range, for example of 1-4.5 MIU/day) due to possible side effects and may be administered subsequently or simultaneously to the inhalation treatment or even may be administered independently if the application of inhalations is not desirable for specific reasons (e.g. if concomitant medication or concomitant diseases do not allow application to the lung). Initially, the injection therapy will also be applied as a standard therapy in determined regular intervals that may be continued depending on the patients need.

The inhalation of the cytokine on an empty stomach may cause mild nausea. Apart from immune modulation in the lung, which per se has an appetite reducing effect, the inhalation causes reactions in the mucosa of the mouth and stomach (in particular, on an empty stomach) and, thus, the appetite reducing effect is enhanced. Inhalation causes, at least temporarily, simultaneous stimulation of the mucosa of the nasopharyngeal space and the oral and gastric cavity. The effect partially correlates with and may inter alia be influenced by the degree of stomach filling. Therapy instructions for optimum administration intended for the patient should take into account the degree of stomach filling if the desired effect is primarily to be an appetite reducing effect.

The administration of cytokines, in particular interleukin-2, interferon-alpha and interferon gamma, leads to a natural reduction of appetite. This is another advantage for smokers since the weight gain associated with quitting smoking may be controlled.

The cytokine, in particular interleukin-2, interferon-alpha and interferon gamma, inhalation therapy for immune modulation may be started according to a controlled scheme. However, if necessary, additional inhalations may be administered. Since the therapy is well-tolerated, it may be increased in intensity and adapted according to individual needs in order to achieve behavior modification. This is another advantage since it is possible to respond to individual problems arising from diurnal rhythm or a pattern of addiction and/or dependence that is not diurnally identical, such as, for example, particularly acute dependence on cigarettes in the morning, food abuse in the evening or during the night, and desires connected with the addictive behavior.

Modern methods for quitting smoking comprise much more than nicotine replacement therapy. They are supported by weight control, diet and psychological assistance. Similarly, methods for treatment of food addiction, alcohol addiction and/or sex addiction may be additionally supported by other treatments. The present invention may be integrated advantageously into modern methods, since essential requirements are fulfilled, such as the induction of indifference towards the desired substance or behavior, high tolerance and compatibility with daily routine, in particular with local administration to the mucosa or inhalation administration as well as of other local administration forms.

In this specification, a number of documents including patent applications and journal publications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

EXAMPLES

The invention will now be described by reference to the following examples, which are merely illustrative and are not to be construed as a limitation of the scope of the present invention.

Example 1

Subcutaneous Administration of Interleukin-2

The patient was a male being treated for tumor therapy and was a moderate smoker and moderately overweight with a slightly increased body mass index of 26.5. The patient was administered one subcutaneous injection of interleukin-2 (aldesleukin) (dose range 1.8-9.0 MIU) once per day. In the first week, the patient received daily subcutaneous injections of 9.0 MIU, however after one week this dose had to be further reduced to 1.8 MIU daily because of lack of tolerability. This dose is well below the approved subcutaneous treatment schedule and only 10-20% of the approved dose, which was intolerable to the patient because of general health. During this comparatively very low dose therapy, there were in the first 10 days only a few influenza-typical concomitant symptoms/reactions, which were controlled by concomitant medication. The patient reported feeling slightly tired. The patient stopped smoking to a large extent during therapy spontaneously. When asked regarding his smoking habit, he stated that, since a few days after the start of the therapy, he had only rarely felt a desire for cigarettes and that his appetite was reduced. The aversion to smoking was retained during the 8 week therapy, even after the dose was reduced and when the very low dose of 1.8 MIU subcutaneous per day was given. The patient reported that he did not smoke at all with the exception of three days (on weekends in company) and that, on these three days, he only sporadically smoked, a maximum of five cigarettes per day, which was significantly fewer cigarettes than what he used to smoke and he did not really have a feeling of a strong need to smoke. Furthermore, due to lack of appetite, the patient lost weight, 1.4 kg, during the therapy. According to the patient, aversion to smoking and reluctance to eat were retained for approximately 2 weeks after the therapy was stopped. Subsequently, his appetite became normal and he was once more tempted to smoke.

Example 2

Subcutaneous Administration of Interferon Alpha

The patient was a male being treated for a progressive, inoperable, urological tumor. The patient smoked up to 2 packs of cigarettes per day and was normal weight. At this point in time he was not smoking but felt a permanent desire for cigarettes. The patient was administered a subcutaneous injection of initially 3×6 MIU interferon alpha (Roferon®) per week for 3 weeks, and then he was administered a reduced dose of up to 3×3 MIU interferon alpha (Roferon) per week for a total treatment time of 3 months. During this therapy, which was considered a comparatively low dose, the patient reports endurable concomitant symptoms such as headache, mild fever and joint pain, which was easily controlled with medicaments. When asked about his smoking behavior, he stated that he did not want to smoke, and that, contrary to the time prior to the therapy, he did not feel the need for cigarettes any longer. Further, he found cigarette smoke unpleasant and his appetite was significantly reduced. It was also not difficult for him to go without smoking. Indifference to cigarettes was retained during the 4 weeks therapy. One week after the 4 weeks of therapy was stopped, the patient stated that he felt the desire to smoke again.

Example 3

Inhalational Administration of Interleukin-2 to a Healthy Female

The patient inhaled a total of 9 MIU interleukin-2 (aldesleukin) per day, in five doses, each of which consisted of 1.8 interleukin-2 (aldesleukin) in 1.5 ml glucose solution, using an aerosol system. Aerosol generation was selected such that the biological effect of the immune modulator was not impeded. The formulation was selected such that the biological activity of interleukin-2 was maintained. The nebulizer produced an aerosol such that it does not impede biological activity and prevents, for example, high temperatures or similar factors from interfering.

Therapy Control:

Measuring the expiratory volume for pulmonary function control by the patient is a suitable means of control for inhalation therapy with interleukin-2. For therapy monitoring, it is advantageous that the patient themselves initially measures the changes caused by the inhalation of interleukin-2 by means of peak flow meter. The peak flow is monitored by a simple measuring device, which allows the control of pulmonary function by the patient themselves. Therapy control using the peak flow meter ensured that the therapeutic aim is achieved with a controlled, acceptable inflammatory reaction of the mucosa. Typically, therapy control can be handed over to the patient to ensure compliance with the withdrawal therapy.

In the present example, the peak flow measurement was carried out prior to the start of the therapy, during therapy and subsequently twice a day. After 7 days, the lowest expiratory volume value (reduced by 20%) was measured in the evening. Even though the therapy was stopped on the seventh day in the evening, the initial values were only measured after a further 7 days indicating a sustained influence on respiratory condition. Peak flow measuring takes the initial values of patients into account; these depend on various parameters and are used to increase treatment (the success and safety of the therapy) when the withdrawal therapy is initiated. As soon as the patient was familiar with the therapy, it was possible to stop measuring or to reduce measuring times significantly.

TABLE 1 peak expiratory flow (PEF) prior to, during (marked grey) and after 7 days of inhalation therapy with IL-2 (in the morning and in the evening)

| Date | 6.7. | 7.7. | 8.7. | 9.7. | 10.7. | 11.7. | 12.7. | 13.7. | 14.7. | 15.7. | 16.7. | 17.7. | 18.7. | 19.7. | 20.7. | 21.7. |
|---|---|---|---|---|---|---|---|---|---|---|---|---|---|---|---|---|
| PEF (1/min) 8.00 a.m. | 500 | 470 | 520 | 490 | 450 | 520 | 420 | 450 | 470 | 450 | 470 | 460 | 470 | 510 | 500 | 500 |
| PEF (1/min) 11.00 p.m. | 440 | 470 | 480 | 470 | 460 | 450 | 400 | 430 | 450 | 460 | 460 | 470 | 480 | 500 | 500 | 500 | a) Effect on the desire for nicotine

The patient smoked occasionally. On the 4th day of the therapy, she reported a strong aversion to nicotine and cigarettes that lasted for the next 10 days and made her avoid rooms in which smokers were present. This was a new phenomenon that was observed for some weeks to follow in a less distinct manner. During this period, the patient was consistently opposed to smoking and did not smoke.

b) Effect on appetite

The patient was normal weight. From the $4^{th}$ day on, the patient felt a desire for light food and an aversion to an opulent diet with high-fat food. Only some days after the therapy was stopped, did her appetite for food of the latter kind begin to return. Reduced food consumption and diet adjustment during therapy were spontaneous.

c) Effect on performance

On day 6, the patient's performance was moderately decreased under stress by physical exertion (jogging).

d) Local and general symptoms

On day 6 of the therapy, a stress-dependent light productive cough was observed that, after stopping the therapy (on day 7), turned into a dry cough that lasted for another 8 days after the therapy was terminated. After one week, a slight increased need for rest was observed. Fever and other concomitant symptoms were not observed. Stopping the therapy after day 7 resulted in a feeling of recovery.

e) Local and systemic measuring parameters during inhalation therapy with interleukin-2

Table 2 reports measurements before, during and after a 7 day course of therapy

TABLE 2

Measuring parameters during inhalation therapy with interleukin-2 (marked grey); the values on day 1 were measured in the morning prior to the start of therapy (Values beyond standard are marked with an asterisk*)

| Date | Normal | 6.7. | 7.7. | 8.7. | 9.7. | 10.7. | 11.7. | 12.7. | 13.7. | 14.7. | 15.7. | 16.7. | 17.7.-18.7 | 19.7. |
|---|---|---|---|---|---|---|---|---|---|---|---|---|---|---|
| Day | | 1 (before start of treatment) | 2 | 3 | 4 | 5 | 6 | 7 | 8 | 9 | | | | |
| Therapeutic Dose (MIU) | | 5 × 1.8 | 5 × 1.8 | 5 × 1.8 | 5 × 1.8 | 5 × 1.8 | 5 × 1.8 | 5 × 1.8 | | | | | | |
| Sputum Eosin. (%) | | 0 | 0 | 2 | | | | 3 | 15 | 7 | | | | |
| Sputum Lymph. (%) | | 6 | 44 | 69 | | | | 23 | 37 | 31 | | | | |
| NO (ppb) | | 25.0 | 28.4 | | 47.0 | | | 72.0 | 47.1 | 51.1 | 43.7 | 45.2 | | 27.1 |
| FEV1 (l) | | 3.88 | 3.73 | | 3.53 | | | 3.26 | 3.51 | 3.71 | 3.72 | 3.53 | | 3.66 |
| Blood Eos (%) | | 0.4 | 1.8 | 2.6 | 2.3 | | | 5.9 | 4.6 | 1.8 | 2.8 | 3.6 | | 1.7 |
| Blood Eos (billion/l) | ≤0.45 | <0.1 | 0.14 | 0.2 | 0.2 | | | 0.5* | 0.32 | 0.1 | 0.2 | 0.2 | | 0.11 |
| Blood Lymph (%) | | 38.2 | 23.4 | 25.6 | 27.6 | | | 17.8 | 32.8 | 40.9 | 43.3 | 42.0 | | 40.5 |
| Blood Lymph (billion/l) | 1.0-4.8 | 2.5 | 1.77 | 1.9 | 2.1 | | | 1.52 | 2.27 | 2.80 | 2.80 | 2.50 | | 2.53 |
| C-reactive Protein (mg/dl) | <5 | <5 | <5 | <5 | <5 | | | 7* | 6* | <5 | <5 | <5 | | <5 |
| Iron (μmol/l) | 11-31 | 19.3 | 19.7 | 25 | 17.2 | | | 10.0* | 10.3* | 12.2 | 11.5 | 12.1 | | 14.5 |

Local inflammatory reactions were observed, such as an increase in eosinophil granulocytes in sputum, an increase in lymphocytes in sputum, an increase in nitric oxide content (gas produced as part of the immune response of monocytes, macrophages and granulocytes) and systemic reactions (increase in eosinophil granulocytes in blood, activation of lymphocytes in blood). An increase in the number of interleukin-2 receptor positive cells in the lung and in blood (not listed in the Table) can also be observed.

f) Summary: After one week of therapy, it was possible to detect the following typical and measurable immune modulations that are associated with the desired behavior modification (e.g., aversion to smoking, high-fat food, excessive food): an increase in eosinophil granulocytes and lymphocytes in sputum and an increase in nitric oxide in the exhaled air (NO). Exclusively local immune modulation resulted in a measured local inflammatory reaction (eosinophils, lymphocytes) but, with increasing therapy duration, also in a detectable light systemic inflammatory reaction (eosinophils and C-reactive protein). In our estimation, the increase in NO was particular suitable for assessing the induction of the desired effect, spontaneous aversion to nicotine and high-fat food, since it can be measured non-invasively. The increase in NO was a measurable concomitant parameter of inhalation aiming at a desired immune modulation. The measurement of peak flow by the patient is an additional useful measurement to monitor the desired immune modulation directly by the patient.

g) The following blood parameters were consistently normal during therapy: haemoglobin, haematocrit, number of erythrocytes, MCV, MCH, EVB, leukocytes, blood platelets, electrolytes (sodium, calcium, potassium, chloride), creatinine, urea, uric acid, bilirubin, total protein, and albumin.

Example 4

Intravesical Administration of Interleukin-2

A male patient and a former smoker having a treatment resistant recurrent carcinoma in situ of the bladder received as an ultimate therapy multiple treatment cycles of intravesical interleukin-2 perfusion of the bladder for 5 days per week, daily dose was 18 MIU per day, given repeatedly until urinary cancer cells disappeared. Therapy was performed similar to previously published interleukin-2 therapy of advanced bladder cancer patients using glycosylated and unglycosylated highly purified interleukin-2 from natural sources (Huland et al Cancer Res (1989) 49, 5469-74). The patient did not experience any evidence of side effects. In urine, the number of eosinophil leukocytes was remarkably increased. Before treatment, no cells positive for IL-2 receptors were found in urine, and no lymphocytes positive for IL-2 receptors were detected in blood. After the first cycle and especially after repeated cycles, a distinct increase in interleukin-2 receptor-positive cells up to 11% occurred, indicating local and subsequent systemic cellular immunomodulation. The absence of any side effects indicated no systemic absorption and this was confirmed as there were no detectable interleukin-2 levels in the blood.

Surprisingly the patient reported, that he experienced a clear aversion to cigarette smoke during and in the days after treatment cycles. This was unusual for him, as he had still a moderate longing for cigarettes.

In this patient even a strictly local (intravesical) bladder mucosal stimulation using interleukin-2 without absorption of interleukin-2 into the blood stream, was sufficient to induce a clear aversion against nicotine addiction.

Example 5

Inhalation Administration of Interleukin-2 for Nicotine Withdrawal

The treatment typically starts with a daily dose of 6-18 Mio IU interleukin-2 (e.g. Aldesleukin) or a comparable dose of another interleukin-2 preparation, divided into several individual doses for inhalation as described in Example 3. The optimum duration of the standard therapy covers the time until the patient is able to spontaneously forgo nicotine. The initial therapy will typically have a duration of 2 to 4 weeks, after which the standard therapy will either be stopped with interleukin-2 being only inhaled if necessary, e.g. when a need for nicotine is felt. The dose can be gradually reduced from e.g. 5 inhalations per day to 4, 3, 2 etc. per day, until the patient inhales interleukin-2 only in the case of need, e.g. in situations typically triggering the need, such as parties. The patient may not need interleukin-2 inhalations for all days between these exceptional situations. In the course of the therapy, the patient determines the time needed for complete withdrawal by effectively suppressing the need for nicotine by inhalation of interleukin-2 as necessary. Heavy smokers may need more time and higher initial doses, more moderate smokers may succeed in shorter time and, on the whole, may need lower doses and shorter therapy periods. If necessary, even after gradual termination of the treatment, an application of multiple daily inhalations may be resumed over a period the patient considers to be necessary to control the desire for nicotine. In principle, the cigarettes the patient would smoke are replaced by the inhalation of interleukin-2 with the interleukin-2 inhalations being continuously reduced and/or the doses are continuously reduced.

In exceptional cases, for example with heavy smokers, the withdrawal may be supported by a systemic injection therapy using low doses interleukin-2 (in the range of 1-4.5 Mio IU/day) due to possible side effects and may be administered subsequently or simultaneously to the inhalation treatment or even may be administered independently if the application of inhalations is not desirable for specific reasons (e.g. if concomitant medication or concomitant diseases do not allow application to the lung). Initially, the injection therapy will also be applied as a standard therapy in determined regular intervals that may be continued depending on the patients need.

Example 6

Inhalation Application of Interleukin-2 for Withdrawal from Excessive Overeating or Consumption of High-Fat, High-Calorie Food The application of the therapy is comparable to the application in Example 3 and differs only in that the patient controls appetite instead of desire for nicotine by inhalation application of interleukin-2. The inhalation of interleukin-2 on an empty stomach may cause mild nausea. Apart from immune modulation in the lung, which per se has an appetite reducing effect, the inhalation causes reactions in the mucosa of the mouth and stomach (in particular, on an empty stomach) and, thus, the appetite reducing effect is enhanced. Inhalation causes, at least temporarily, simultaneous stimulation of the mucosa of the nasopharyngeal space and the oral and gastric cavity. The effect partially correlates with and may inter alia be influenced by the degree of stomach filling. Therapy instructions for optimum application intended for the patient should take into account the degree of stomach filling if the desired effect is primarily to be an appetite reducing effect.

Example 7

Further Applications of Interleukin-2

Further applications of interleukin-2 which induce an immune modulation of the mucosa of the respiratory tract or the gastro-intestinal tract causing a comparable proliferation of lymphocytes, eosinophils and/or causing in particular an increase in nitric oxide (NO) as in Example 3 may comprise oral/buccal application or intake of interleukin-2 and other cytokines (in the form of tablets, pastilles, chewing gums, lozenges, gargle solutions, juice preparations, etc.), nasal intake of interleukin-2 (nasal spray, nasal suspension, etc.) also in local slow release forms or specific application forms such as nano- or micro-needle injection systems which are introduced in the mucosa of the oral, gastrointestinal, nasal, pharyngeal or respiratory regions and even in the mucosa of the genitourinary tract.

The invention claimed is:

1. A method for treating nicotine addiction or reducing food consumption in a patient in need thereof, comprising mucosally administering to the patient a therapeutically effective amount of a cytokine, wherein the cytokine is interleukin-2.

2. The method of claim 1, wherein the patient is in need of treatment for nicotine addiction.

3. The method of claim 1, wherein the patient is in need of reducing food consumption.

4. The method of claim 1, wherein the cytokine is stabilized.

5. The method of claim 1, wherein the cytokine is substantially pure.

6. The method of claim 1, wherein the mucosal administration is selected from the group consisting of administration onto the respiratory tract, administration onto the gastrointestinal tract, intravesical administration and intravaginal administration.

7. The method of claim 6, wherein the administration onto the respiratory tract is nasal administration.

8. The method of claim 6, wherein the administration onto the gastrointestinal tract is selected from the group consisting of oral administration, buccal administration or rectal administration.

9. The method of claim 6, wherein the cytokine is administered by inhalation.

10. The method of claim 1, wherein the cytokine is administered at a dose in the range of 0.0001 MIU to 54 MIU per day.

11. The method of claim 1, wherein the cytokine is administered at a dose in the range of 0.0001 MIU to 36 MIU per day.

12. The method of claim 1, wherein the cytokine is administered at a dose in the range of 0.1 MIU to 18 MIU per day.

13. The method of claim 1, wherein the cytokine is administered at a dose in the range of 1 MIU to 9 MIU per day.

14. The method of claim 1, wherein the cytokine is administered at a dose in the range of 10 ng to 3.3 mg per day.

15. The method of claim 1, wherein the cytokine is administered at a dose to increase nitric oxide in air exhaled by the patient; increase the number of eosinophil granulocytes in the bronchoalveolar system; or increase the number of interleukin-2 receptor positive cells in the bronchoalveolar system.

16. The claim 1, wherein the cytokine is administered as a daily dose that is divided into 2 or more portions per day or divided into from 1 to 10 portions per day.

17. The method of claim 1, wherein the cytokine is administered in combination with one or more flavoring agents.

\* \* \* \* \*

UNITED STATES PATENT AND TRADEMARK OFFICE
CERTIFICATE OF CORRECTION

| | | |
|---|---|---|
| PATENT NO. | : 9,028,808 B2 | Page 1 of 1 |
| APPLICATION NO. | : 13/574106 | |
| DATED | : May 12, 2015 | |
| INVENTOR(S) | : Edith Huland | |

It is certified that error appears in the above-identified patent and that said Letters Patent is hereby corrected as shown below:

In title page, item (30) Foreign Application Priority Data, delete "1015197" and insert --10151979.1-- therefor.

Signed and Sealed this
Twentieth Day of October, 2015

Michelle K. Lee
*Director of the United States Patent and Trademark Office*